(12) United States Patent
McDevitt et al.

(10) Patent No.: US 9,671,413 B2
(45) Date of Patent: Jun. 6, 2017

(54) PROSTATE CANCER POINT OF CARE DIAGNOSTICS

(75) Inventors: John T. McDevitt, Houston, TX (US); Nicolaos Christodoulides, Houston, TX (US); Pierre N. Floriano, Missouri City, TX (US); Ian Thompson, San Antonio, TX (US)

(73) Assignees: William Marsh Rice University, Houston, TX (US); Board of Regents of the University of Texas System, Austin, TX (US)

( * ) Notice: Subject to any disclaimer, the term of this patent is extended or adjusted under 35 U.S.C. 154(b) by 516 days.

(21) Appl. No.: 13/884,195

(22) PCT Filed: Nov. 11, 2011

(86) PCT No.: PCT/US2011/060307
§ 371 (c)(1),
(2), (4) Date: Jun. 21, 2013

(87) PCT Pub. No.: WO2012/065025
PCT Pub. Date: May 18, 2012

(65) Prior Publication Data
US 2013/0274136 A1 Oct. 17, 2013

Related U.S. Application Data

(60) Provisional application No. 61/412,994, filed on Nov. 12, 2010.

(51) Int. Cl.
*G01N 33/68* (2006.01)
*G01N 33/574* (2006.01)
(Continued)

(52) U.S. Cl.
CPC ..... *G01N 33/689* (2013.01); *G01N 33/54386* (2013.01); *G01N 33/57434* (2013.01); *C40B 40/10* (2013.01)

(58) Field of Classification Search
None
See application file for complete search history.

(56) References Cited

U.S. PATENT DOCUMENTS 6,589,779 B1    7/2003   McDevitt
6,602,702 B1    8/2003   McDevitt
(Continued)

FOREIGN PATENT DOCUMENTS

WO    2004009840    1/2004
WO    2005083423    9/2005
(Continued)

OTHER PUBLICATIONS

Goodey et al., Development of Multianalyte Sensor Arrays Composed of Chemically Derivatized Polymeric Microspheres Localized in Micromachined Cavities, J. Amer. Chem. Soc., 123(11):2559-2570, 2001.
(Continued)

*Primary Examiner* — Kaijiang Zhang
(74) *Attorney, Agent, or Firm* — Boulware & Valoir

(57) ABSTRACT

The invention relates to point of care diagnostic disposables, devices, methods, and systems for diagnosing or predicting prostate cancer. The present invention employs biomarker specific reagents in disposable cassettes or lab cards for use as analyzers, as well as software to evaluate and report test results. The system promises to improve point of care in vitro diagnostics.

10 Claims, 9 Drawing Sheets

(51) Int. Cl.
*G01N 33/543* (2006.01)
*C40B 40/10* (2006.01)

(56) References Cited

U.S. PATENT DOCUMENTS

| | | |
|---|---|---|
| 6,649,403 B1 | 11/2003 | McDevitt |
| 6,680,206 B1 | 1/2004 | McDevitt |
| 6,713,298 B2 | 3/2004 | McDevitt |
| 6,908,770 B1 | 6/2005 | McDevitt |
| 7,022,517 B1 | 4/2006 | McDevitt |
| 7,316,899 B2 | 1/2008 | McDevitt |
| 7,491,552 B2 | 2/2009 | McDevitt |
| 7,651,868 B2 | 1/2010 | McDevitt |
| 7,781,226 B2 | 8/2010 | McDevitt |
| 8,101,431 B2 | 1/2012 | McDevitt |
| 8,105,849 B2 | 1/2012 | McDevitt |
| 8,257,967 B2 | 9/2012 | McDevitt |
| 8,377,398 B2 | 2/2013 | McDevitt |
| 2004/0053322 A1 | 3/2004 | McDevitt |
| 2005/0136548 A1 | 6/2005 | McDevitt |
| 2006/0073585 A1 | 4/2006 | McDevitt |
| 2006/0211059 A1 | 9/2006 | Taneja |
| 2006/0228256 A1 | 10/2006 | McDevitt |
| 2006/0257854 A1 | 11/2006 | McDevitt |
| 2006/0257941 A1 | 11/2006 | McDevitt |
| 2006/0257991 A1 | 11/2006 | McDevitt |
| 2008/0038738 A1 | 2/2008 | Weigum |
| 2008/0050830 A1 | 2/2008 | Floriano |
| 2008/0219891 A1 | 9/2008 | McDevitt |
| 2008/0300798 A1 | 12/2008 | McDevitt |
| 2009/0215072 A1 | 8/2009 | McDevitt |
| 2009/0258791 A1 | 10/2009 | McDevitt |
| 2010/0291588 A1 | 11/2010 | McDevitt |
| 2011/0251075 A1 | 10/2011 | McDevitt |
| 2012/0208715 A1 | 8/2012 | McDevitt |
| 2013/0130933 A1 | 5/2013 | McDevitt |

FOREIGN PATENT DOCUMENTS

| | | |
|---|---|---|
| WO | 2005085796 | 9/2005 |
| WO | 2007002480 | 1/2007 |
| WO | 2012021714 | 2/2012 |
| WO | PCT/US2011/060307 | 5/2012 |

OTHER PUBLICATIONS

Christodoulides et al., Application of microchip assay system for the measurement of C-reactive protein in human saliva Lab. Chip, 5(3):261-9, 2005.

Thompson IM, et al., "Prevalence of Prostate Cancer among Men with a Prostate Specific Antigen Level ≤4.0 ng per Milliliter" New Engl J Med, 2004; 350:2239-46.

Thompson IM, et al., Assessing prostate cancer risk: results from the Prostate Cancer Prevention Trial; J Natl Cancer Inst., 2006; 98:529-34.

Ankerst DP, et al. Predicting prostate cancer risk through incorporation of prostate cancer gene 3; J Urology, 2008;180:1303-8.

Jesse V. Jokerst et al., Programmable Nano-Bio-Chip Sensors: Analytical Meets Clinical, Analytical Chemistry, vol. 82, No. 5, Mar. 1, 2010.

Chun et al, "Prostate Cancer Gene 3 (PCA3): Development and Internal Validation of a Novel Biopsy Nomogram," European Urology, 56(2009) 659-668.

Regency Medical Policy Manual for Genetic Testing, Effective Date Jan. 1, 2013.

Bourdoumis et al., "The Novel Prostate Cancer Antigen 3 (PCA3) Biomarker," International Braz J Urol, Nov./Dec. 2010, 36(6):665-669.

Soluble Analyte Profiler (SAP) Lab Card

Key card components
1. Sample entry port
2. Pinch valve
3. Buffer entry port
4. Blister
5. Bubble trap
6. Reagent port
7. Waste reservoir
8. Waste reservoir external vent
9. Bead support chip
10. Port to external waste containment (chip housed in detection window)

PROSTATE CANCER POINT OF CARE DIAGNOSTICS

PRIOR RELATED APPLICATIONS

This application is a National Phase filing under 35 U.S.C. §371 of International Application PCT/US11/60307, filed on Nov. 11, 2011, which claims priority to U.S. Provisional Application 61/412,994, filed Nov. 12, 2010. Both applications are expressly incorporated by reference in its their entirety.

FEDERALLY SPONSORED RESEARCH STATEMENT

None.

FIELD OF INVENTION

The invention relates to point of care diagnostic disposables, devices, methods, and systems for diagnosing or predicting prostate cancer.

BACKGROUND OF THE INVENTION

Prostate cancer is a form of cancer that develops in the prostate, a gland in the male reproductive system. Most prostate cancers are slow growing; however, there are cases of aggressive prostate cancers, where the cancer cells metastasize (spread) from the prostate to other parts of the body, particularly the bones and lymph nodes. Prostate cancer may cause pain, difficulty in urinating, problems during sexual intercourse, or erectile dysfunction, and other symptoms can potentially develop during later stages of the disease.

Rates of detection of prostate cancers vary widely across the world, with South and East Asia detecting this cancer less frequently than in Europe and especially the United States. Prostate cancer tends to develop in men over the age of fifty and although it is one of the most prevalent types of cancer in men, many never have symptoms, undergo no therapy, and eventually die of other causes. However, prostate cancer accounts for approximately 15 percent of all cancer cases in the United States and 15 percent of male cancer deaths. Further, the total cost of treating prostate cancer in the U.S. amounts to several billion dollars per year. Since most men diagnosed with the disease are over age 65 years of age, most of the cost is paid for through Medicare. Thus, although a slow growing cancer, prostate cancer has profound implications for society, and it would be beneficial to detect and treat aggressive cancers as early as possible.

The presence of prostate cancer may be indicated by symptoms, physical examination (e.g., by digital rectal examination or DRE), assay for cancer markers, and/or biopsy. The most widely used and successful serum marker for prostate cancer is prostate-specific antigen (PSA). One reason for the success of this protein as a serum marker is that PSA is present in the prostate tissues at 1 mg per cc of tissue, but is almost undetectable in the serum of men with healthy prostates. The presence of elevated PSA in the serum is thus indicative of prostate trauma or some type of prostate disease.

However, one shortcoming of PSA is that it is also elevated in benign prostate diseases such as BPH and prostatitis. Therefore, efforts to improve the diagnostic utility of PSA have been undertaken, and improvements have come from an understanding of the various molecular forms of PSA in the serum.

It was initially assumed that the PSA measured in the serum was the natural 33 kDa form of the protein containing 237 amino acids. It was only later discovered that PSA in the serum is mostly covalently attached to the serum protease inhibitor alphal-antichymotrypsin (ACT) and that only a relatively minor portion of the PSA was present as the non-complexed form. Thus, the terms "free" PSA (FPSA or free-PSA) and "complexed" PSA (cPSA) are now used to distinguish non-complexed from complexed PSA.

Immunoassays have long been developed to distinguish free and total PSA (free plus complexed PSA) and it is known that a lower ratio of free-PSA correlates with a higher risk of prostate cancer. By contrast, a higher percentage of free-PSA correlates with benign disease such as BPH. Since that discovery, different PSA antibodies have been developed that can distinguish free-PSA from cPSA and total PSA, some of which have been applied in clinical studies.

More recently, the molecular forms of PSA have expanded beyond free and complexed PSA to include the sub-forms of free-PSA-BPSA and pro-PSA. The biomarker BPSA is a form of free-PSA that is identical to native mature PSA, contains 237 amino acids like PSA, but has 2 internal peptide bond cleavages at Lys182 and Lys145. BPSA is elevated in the prostate transition zone and is associated with benign prostatic hyperplasia (BPH), whereas most cancers are in the periphery zone. Pro-PSA is the zymogen form of PSA and increases in cancer. Because BPSA and pro-PSA are associated with opposing disease states in the prostate, they are sometimes referred to as the yin and yang of PSA forms. Together these forms represent individual forms of free-PSA that are more disease-specific than free-PSA or cPSA.

Although the PSA-based tests have improved over time, there is still a need in the art for simple, reliable diagnostic tests for prostate cancer that can be applied in any convenient setting, including for example, retail outlets or drug stores. The ideal test would be reliable, very sensitive, and, in combination with input about various risk factors, be able to differentiate between the various prostate diseases and allow the patient to make informed choices about what next steps, if any, should be taken to address prostate problems.

SUMMARY OF INVENTION

The invention generally relates to point of care diagnostics for prostate cancer, disposable cassettes or lab cards containing biomarker specific reagents, portable devices for use as analyzers or drivers with same, software to evaluate and report test results, and the overall diagnostics and reporting system as a whole.

Generally speaking, a patient's, age, race, family history, DRE results, biopsy results, and other risk factors are collected, along with biological samples, such as serum, saliva or urine samples. The samples are then applied to the disposable cassette, which is inserted into a slot for receiving same in a portable device that contains the fluidics, electronics, power, software, image detection and analysis components, and the like, needed to implement the test. The relevant patient information is also inputted into the device, the assay run, the results collected, and the embedded software compiles the various data into a risk index, as described below. The output from the device can be displayed, printed as a report, or stored, and either further analyzed or communicated to another computer or bioinformatics system, as desired.

The system promises to improve point of care in vitro diagnostics and is called herein a "Programmable Bio-Nano- Chip" system. The "programmable" feature of the system refers to the capacity of the sensor ensemble to function as a standard platform that can be re-tasked (i.e. re-programmed) to serve a new application through insertion of molecular level code (i.e. biomarker-specific reagents). The "Bio" terminology refers to the capacity to measure and extract the bio-signatures associated with the disease progression. The "Nano" element describes the capacity to miniaturize the system which is embodied in the use of nano-nets for efficient and rapid biomarker capture, as well as quantum dots for increased signal generation. The "Chip" term emphasizes the capacity to mass produce the sensor elements (array chips) in way analogous to those used by the microelectronics industry that ultimately lead to high performance at reduced cost.

The same sensor platform has the capacity to measure both soluble analytes using bead microreactors, as well as cell counting, typing, and differentiation using membrane microstructures. These two distinct types of assay platforms are packaged within a disposable, single-use disposable cartridge (or cassette or lab card) (FIG. 1). The lab card with built-in excipient-stabilized detection reagents, fluid mixing and partitioning compartments, including a sample loading dock and self-contained bio-waste compartment, is inserted in the light emitting diode (LED)/charged coupled device (CCD)-equipped mechano-optical analyzer to complete entire assay sequences in an automated manner.

The "toaster"-sized portable analyzer serves as a universal interface, portable smart device that includes a fully embedded PC. It also provides for fluidic, mechanical, optical, and software capabilities operated through a user interface with functionality beginning with the insertion of the lab card into a slot for same and ending with an easy to interpret liquid crystal display (LCD) readout of the test result.

Compared to gold standard methods, such as enzyme-linked immunoassay (ELISA), the P-BNC system exhibits assay times in minutes instead of hours, limits of detection (LOD) two or more orders of magnitude lower, and a proven capacity to multiplex 10 or more concurrent analytes with appropriate internal controls and calibrators. For example, salivary biomarkers that were previously undetectable by standard methods, may now be targeted with the portable testing devices to assess systemic disease in a non-invasive fashion. Examples of such devices are set forth in Goodey et al., J. Amer. Chem. Soc., 123(11):2559-2570, 2001, and Christodoulides et al., Lab. Chip, 5(3):261-9, 2005b, the entire contents of which are incorporated by reference into this application.

The strong analytical performance of the P-BNC system may be attributed to the porous nature of its agarose bead sensors, the active transport mode of delivery of the sample and detection reagents, as well as the highly stringent washes associated with this micro-fluidic approach. Like ELISA, the bead-based P-BNCs complete two-site immunometric, as well as competitive, immunoassays; however, unlike ELISA, which limits the diffusion-mediated antigen (Ag)-Antibody (Ab) binding to a 2-dimensional, planar surface at the bottom of the well, the P-BNC cards provide a ~1,000 to 10,000-fold increase in surface area on the 3-dimensional bead or disk sensor. This 3-dimensional reactor allows for significantly increased contact area, as well as on, off and then on again, higher avidity Ag-Ab interactions. All of the afore-mentioned features contribute to the generation of high signal-to-noise ratios, which ultimately translate into the advanced detection capabilities associated with the P-BNC system.

In certain embodiments, the invention is directed to a disposable cartridge, cassette, or lab card, wherein the testing sites comprise agarose substrates (beads or disks) that are conjugated to either target or anti-target antibody, and thus serves in competitive or sandwich two-site immunometric assays.

The disposable lab card also contains channels and other microfluidics, such that fluid can be forced to pass through the agarose beads or disk. Blister packs or other chambers can also be placed on the disposable cartridge and can contain, e.g., wash fluids, reagent fluids, and the like. Channels designed for mixing and fluid flow permeate this architecture, and manipulations of the fluidic cartridges reconstitute and disperse reagents through the labcard. Linear actuation controls all fluid motion via pressure actuation steps provided by the analyzer device. These cards are not detailed herein, but are described more fully in U.S. Ser. Nos. 61/484,492, filed May 10, 2011, and 61/558,165, filed Nov. 10, 2011, and each expressly incorporated by reference in its entirety for all purposes.

The cards are constructed from common, inexpensive materials, including vinyl adhesive, laminate, stainless steel, and poly-(methyl methacrylate) (PMMA). Computer-aided design (CAD) models the cards, and then a CAD plotter/cutter incises the vinyl. Up to seven layers of vinyl/laminate are deposited on six to eight cards using conventional, parallel layering methods. Cards are disposable and purposed to service one patient and a single assay. The lab cards may also be prepared from a three-layer plastic stack prepared by injection molded plastic methods. These three layers are sealed into a single coherent part using laser sealing procedures or various adhesive layers.

The agarose can be plain agarose, or any of the agarose derivatives such as cross-linked agarose, sepharose, or any agarose derivatives that can be used for affinity chromatography. The array can be on agarose beads or disk, as discussed above. Where disks are employed, the disk is preferably about 10-50 um thick and 50-200 um in width, but larger or smaller sizes are also possible, depending on sample size, specificity of the reagents, and the sensitivity of the instrumentation.

In some embodiments, the disk sits on a porous support or substrate, and the fluidics are such that fluid is forced through the disk. The porous substrate can be any membrane, such as nitrocellulose membrane, or poly(methyl methacrylate) (pmma) membrane. It can also be a more substantive support, such as porous glass, ceramic, plastic (delrin, pmma, acrylonitrile butadiene styrene, i.e. Abs), or metallic (e.g., stainless steel) frit. In other embodiments, the disk can sit in a well, and the fluids merely pass over the disk in the same way they would a bead. Where wells are used, either a plastic, glass, silicon, or stainless steel chip arrayed with wells, each of which hosts an individual bead or disk sensor, is used to complete the disposable cartridge.

These arrays of antibodies can be easily exchanged, by substituting a new array on the lab card, thus quickly and easily reprogramming the card for a new assay. The reprogramming can be completed, by uploading assay specific software to the analyzer device, via e.g., USB, and/or by providing different reagents and fluids in the blister packs or chambers or in dry reagent pads as needed.

Generally, the disposable cartridges or lab cards comprise a detection or analysis window, which can be covered with a transparent cover such as glass, polycarbonate, acrylic, and the like, under which is housed the array of agarose beads or disks. The cover is optional, particularly where the array chip is added by the user at the time of the test. However, if the array chip and lab card are preassembled for sale, a cover can be beneficial as it prevents the array chip containing the agarose beads from getting dehydrated. The capture antibody conjugated beads are prepared in batches and are stored until use, with a demonstrated long-term stability. Preferably a common detector antibody is contained in an upstream chamber in a dry form (e.g., in a dry porous pad) along with excipients to promote long term stability.

A sample is applied to the card via a specimen entry port, and the sample travels to the detection window where the arrayed capture antibodies capture the analyte of interest. Wash fluid (e.g., PBS or PBS plus detergent) from a blister pack on the card is then activated, and travels to the array to wash away unbound sample. Next, PBS or other appropriate buffer is released and en route to the analysis window collects and reconstitutes the detection antibody, which will then stain the captured analytes on the beads or disks. Additional wash solution follows to wash off unbound detector antibody. A waste chamber downstream of the array collects all waste fluids leaving the array.

Purified calibration standards in the array are first analyzed to derive the standard curves to which tested clinical samples are compared. Dedicated image analysis algorithms convert fluorescent signals from the sample into quantitative measurements of free-PSA, complexed PSA and total PSA, through interpolation of signals developed from testing of samples on a dose curve generated the purified calibration standards. These values are then used, together with any patient information that was inputted into the device to prepare and report a risk of prostate cancer, and if indicated, a risk of high grade prostate cancer.

Compared with gold standard systems, such as enzyme-linked immunoassay (ELISA), the P-BNC system has assay times measured in minutes rather than hours, limits of detection (LOD) two or more orders of magnitude lower, and multiplex capacity of 10 or more concurrent analytes with appropriate internal controls.

Our initial proof of concept studies validated a test device comprising agarose beads with PSA and free-PSA specific antibodies conjugated thereto, but many markers can be added to the device and further improve its accuracy and diagnostic value. Additional markers that can be incorporated into the device are discussed below.

CEA (Carcinoembryonic antigen) is a cell-surface fetoprotein expressed by many different tumor types, including poorly differentiated prostate cancer. Prior to the advent of PSA elevated CEA was found in 30% of newly diagnosed prostate cancers. Moderately elevated CEA concentrations have been found only in patients with either "pure" or "predominantly" hormone insensitive disease (without soft tissue lesions) and particularly after suppression of hormone sensitive cell subpopulations.

CGA (Chromogranin A, also CGB, CGC, etc.). These markers are products of the tumor cell population and sometimes are clues as to the tumor taking on an identity that is associated more with certain clinical behavior, such as small cell prostate cancer. Such small cell tumors grow faster, involve liver, lung and lymph nodes in unusual sites, frequently don't express much PSA and have lytic bone lesions instead of dense blastic lesions, etc. CGA is an excellent marker for neuroendocrine tumors, particularly nonfunctioning tumors, and the measurement of CGA is also useful to detect prostatic carcinoma in patients whose PSA is not elevated.

DNA-Ploidy Tests performed on biopsy samples are reported as DIPLOID—e.g., having one complete set of normally paired chromosomes (normal). Diploid cancer cells tend to grow slowly and respond well to hormone therapy. ANEUPLOID means having an abnormal number of sets of chromosomes and TETRAPLOID, means having two paired sets of chromosomes, which is twice as many as normal. Aneuploid cancer cells tend not to respond well to hormone therapy. Ploidy can be assessed with a DNA stain on a per cell basis.

DHEA (dehydroepiandrosterone) is an adrenal androgen. DHEA levels decline with age, yet prostate gland enlargement and cancers increase with age. It is possible that DHEA, being a weak androgen, can actually attach to and block testosterone or DHT receptors on prostate tissue, thus preventing the influence by more powerful androgens DHT (dihydrotestosterone). 5-alpha-dihydrotestosterone is the male hormone which is most active in the prostate. It is made when an enzyme (5-alpha reductase) in the prostate stimulates the transformation of testosterone to DHT. There are reports that DHT is as much as 4× more active in prostate cancer than testosterone. Proscar (finasteride) is considered a potent 5-alpha reductase inhibitor and is often prescribed as part of a complete androgen blockade.

NSE: (Neuron-specific enolase) is a specific marker for neuroendocrine tumors which express proteins or enzymes that are reflective of a de-differentiated tumor cell population such as small cell prostate cancer. When both CGA and NSE are elevated the prognosis is considered poor.

PAP (Prostatic acid phosphatase) is a blood enzyme whose levels may be elevated in patients with prostate cancer that has invaded or metastasized elsewhere. PAP is not elevated unless the tumor has spread outside the anatomic prostatic capsule. A persistently elevated serum PAP is considered evidence of metastasis, but only 75% of patients with metastasis have an elevated PAP. In a study at the Johns Hopkins University School of Medicine, 21 of 460 men or 4.6% had elevations of PAP. Of those men fully evaluated evidence of extraprostatic disease was documented in all. Positive bone scans, extraprostatic extension of disease, PSA>100, positive lymph nodes and positive seminal vesicles were found. Most of the above patients with increased PAP's (17 of 21) had abnormal DRE's consistent with disease outside of the prostate or PSA's>100. Therefore, in these patients the PAP was not that helpful. In the remaining 4 patients, the PAP was helpful in directing treatment towards systemic therapy as opposed to local therapy. A PAP determination as part of the initial staging evaluation is still reasonable. In addition, in some patients PSA may be normal or zero while the PAP is elevated, leaving PAP to be the only remaining biologic marker that can be followed.

PCA3 (Prostate cancer antigen 3, also referred to as DD3) is a urine-based biomarker. Compared to serum PSA, PCA3 has a lower sensitivity but a higher specificity and a better positive and negative predictive value. It is independent of prostate volume, whereas PSA is not, and should be measured in the first portion of urine after prostate massage with digital rectal examination (DRE). PCA3 has been shown to be useful to predict the presence of malignancy in men undergoing repeat prostate biopsy. This means that it could be useful clinically for a patient for whom DRE and PSA suggest possible prostate cancer, but the first prostate biopsy returns a normal result. This occurs in approximately 60% of cases, and on repeat testing, 20-40% have an abnormal biopsy result. Other uses that are being studied for PCA3 include its correlation with adverse tumor features such as tumor volume, grading (Gleason score) or extracapsular extension, but these studies have so far produced conflicting results.

PSA (Prostate Specific Antigen) is a protein secreted by the epithelial cells of the prostate gland, including cancer cells. An elevated level in the blood indicates an abnormal condition of the prostate gland, either benign or malignant. PSA is used to detect potential problems in the prostate gland and to follow the progress of treatment. PSA is currently used as a specific diagnostic marker for the early detection of prostate cancer and to separate patients with tumors from those without tumors.

FPSA (Free-PSA) analysis sometimes called "PSA-II" (Prostate-Specific Antigen type II) reports the percentage of free-PSA to total-PSA (total-PSA=free-PSA+c-PSA) and is helpful for screening purposes when PSA values are above the normal threshold for an age group and less than 10; one study showed that men with PSA II>25% had no cancer; those with <10% were likely to have prostate cancer. BPSA and pro-PSA can be individually assessed as well as free-PSA.

PSADT (PSA Doubling Time) has been evaluated in patients with a rising PSA after local treatment with either radical prostatectomy (RP) or radiotherapy (RT). In these settings PSADT has been shown to be significantly shorter in those patients who developed metastases than in those who did not develop metastatic disease. If the PSADT is <10 months there is a high probability of metastatic disease. Patients post-RP with this finding would not be good candidates for local RT; however patients with a long PSADT would be such candidates. Patients post-RT with a short PSADT have a high likelihood of metastatic disease, whereas those with a long PSADT might be candidates for salvage cryosurgery.

PSA RT-PCR: PSA (Reverse Transcriptase-Polymerase Chain Reaction) is a blood test that detects micrometastatic cells circulating in the blood stream and may be useful as a screening tool to help avoid unnecessary invasive treatments (RP, RT, etc.) on patients with metastasized prostate cancer. Although not FDA approved, it is available at locations where FDA approved clinical trials of the test are being done.

Prolactin (PRL) is a trophic hormone produced by the pituitary that increases androgen receptors and increases sensitivity to androgens. Prolactin modulates prostatic androgen uptake, affects its intracellular metabolism and utilization, and thereby promotes differentiation, growth and secretory function of the prostate. Many but not all men treated with hormone manipulations develop elevated prolactin levels and men who develop hyperprolactinemia during estrogen, diethylstilbestrol, cyproterone or estramustine treatment have been reported to have a much higher rate of disease progression and death from prostate cancer. It has been theorized that prolonged prolactin stimulation from long-term hormone therapy could play role in the onset of androgen resistant tumors.

Pyrilinks-D is a laboratory test that measures deoxypyridinoline (Dpd), a specific marker of bone resorption (loss), which is excreted unmetabolized in urine. It can be used to support the decision to initiate antiresorptive therapy and track changes in bone resorption rates in response to therapy. If Dpd levels are higher than 5.4 in men, the patient is experiencing accelerated bone resorption and may be at increased risk of bone loss. The test is usually run to establish a base line and then at 3 to 6 month intervals to monitor therapy.

Testosterone (T) is the male hormone or androgen that comprises most of the androgens in a man's body. Chiefly produced by the testicles, it is essential to complete male sexual function and fertility. Since there are different ways of reporting testosterone, it is important to give the units as either ng/dl or nM/Liter. nM/L×28.8=ng/dl (multiple ng/dl by 0.0347 to get nM/L).

Other markers are being validated for use in prostate cancer diagnosis, and the above list is not intended to be exclusive.

The following abbreviations are used herein:

| Abbreviations | |
| --- | --- |
| Ab | Antibody |
| ABS | Acrylonitrile butadiene styrene |
| AUC | Area under the curve |
| BM | Biomarker |
| BMI | Body mass index |
| BPH | Benign prostate hyperlplasia |
| BPSA | A form of free-PSA that is identical to native mature PSA, contains 237 amino acids like PSA, but has 2 internal peptide bond cleavages at Lys182 and Lys145 |
| CAB | Complete androgen blockade |
| CCD | Charge coupled device |
| CEA | Carcinoembryonic antigen |
| CGA | Chromogranin A |
| cPSA | Complexed PSA |
| CV | coefficient of variation |
| DHEA | Dehydroepiandrosterone |
| DHT | dihydrotestosterone |
| DNA | Deoxyribonucleic acid |
| Dpd | xypridinoline |
| DRE | Digital rectal exam |
| FPSA | Free-PSA |
| LOD | Limits of detection |
| MAB | Monoclonal Ab |
| NPV or PV | Negative predictive value |
| NSE | Neuron-specific enolase |
| PMMA | Poly(methyl methacrylate) |
| PPV or PV+ | positive predictive value |
| pro-PSA | the zymogen of PSA |
| PSA | Prostate specific antigen, aka gamma-seminoprotein or kallikrein-3 (KLK3) |
| PV | Predictive value |
| RNA | Ribonucleic acid |
| ROC | Receiver operating characteristic. A graphical plot of the sensitivity, or true positive rate, vs. false positive rate (1—specificity or 1—true negative rate), for a binary classifier system as its discrimination threshold is varied. The ROC can also be represented equivalently by plotting the fraction of true positives out of the positives (TPR = true positive rate) vs. the fraction of false positives out of the negatives (FPR = false positive rate). Also known as a Relative Operating Characteristic curve, because it is a comparison of two operating characteristics (TPR & FPR) as the criterion changes. |
| RP | Radical prostectomy |
| RT | Radiation therapy |
| SS | stainless steel |
| T | Testosterone |
| tPSA | Total PSA |

The word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the invention.

DETAILED DESCRIPTION OF THE INVENTION

Figure 1A:
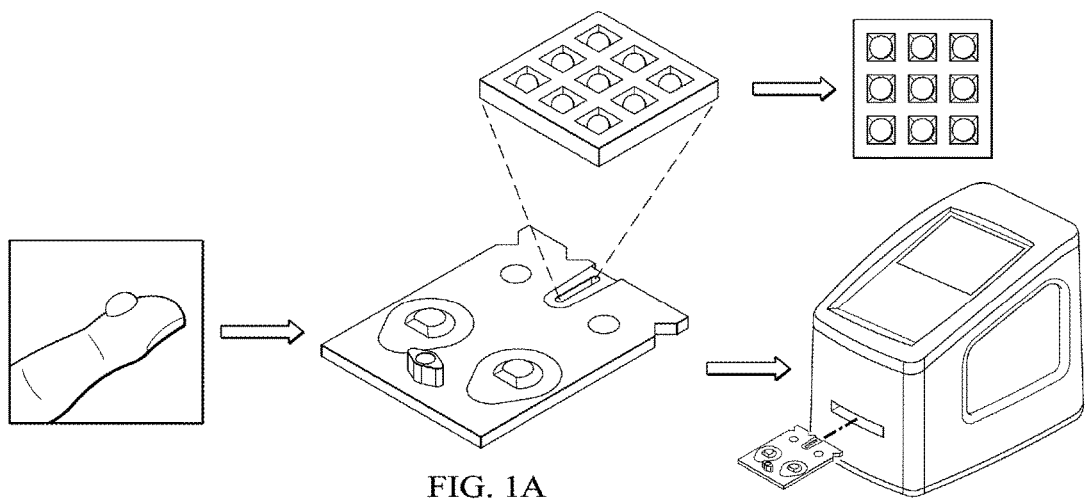
FIG. 1a. The complete p-bnc point of care testing system includes the microfluidic, bead-hosting disposable cartridge (aka cassette or lab card) and the analyzer needed to simultaneously quantitate the levels of a panel of prostate cancer biomarkers to yield a multi-marker prostate cancer signature using a fingerstick amount of blood.
Figure 1B:
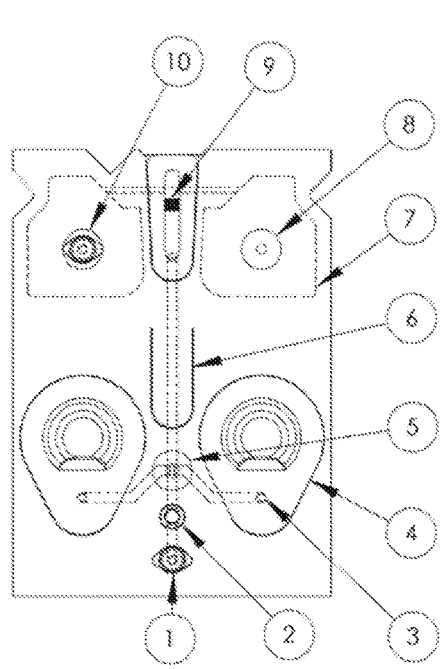
FIG. 1B showing an exemplary disposable card with detection window housing an exchangeable array chip having an array of e.g., agarose beads thereon conjugated to various antibodies.

Although the prostate cancer test can be used with any type of diagnostic assay that provides sufficient sensitivity, a preferred test uses "sandwich"-type of immunoassays for PSA, free-PSA and pro-PSA or complexed PSA analytes. This assay format is based on the binding of analyte to a capturing antibody immobilized on beads, and its subsequent detection by a second antibody conjugated to a stable fluorescent dye. These are called "capture" and "detection" antibodies herein.

Table 1 shows the test antibody reagents as well as protein standards used in the initial proof of concept assays. Capture antibodies were coupled to agarose beads via reductive amination, while detection antibodies were conjugated to AlexaFluor®488 using a conjugation kit from Molecular Probes. Protein standards were used for proof of concept experiments as well as for the development of calibration curves for each assay.

TABLE 1

Assay reagents applied in the assays for PSA, free-PSA and pro-PSA.

| Biomarker | Capture Antibody To be coated on bead sensors | Detection Antibody To be conjugated to Alexafluor488 | Standard Antigen For proof of concept ad dose curve |
|---|---|---|---|
| PSA | M165-mAb (CalBioReagents) | M164-mAb (CalBioReagents) | Human PROSTATE SPECIFIC ANTIGEN Native, cat# 7820-0504 (AbD Serotec) |
| | Mouse Anti-Prostate Specific Antigen (PSA) Monoclonal Antibody, Clone M212091, Cat# 10-P20C (Fitzgerald) | Mouse Anti-Prostate Specific Antigen (PSA) Monoclonal Antibody, Unconjugated, Clone M612152, Cat# 10-P20G (Fitzgerald) | Human PSA, Cat. # CS114702 (Cell Sciences) |
| | Rabbit Anti-PSA Polyclonal Antibody, CAT# GTX19554 (GeneTex) | Rabbit Anti-Human PSA Polyclonal Antibody, Cat# 18-272-196790-1 mg, (GenWay) | Human PROSTATE SPECIFIC ANTIGEN, cat# 10-783-79624-0.2 mg, GenWay |
| % free-PSA | Mouse Anti-Human Free-PSA Monoclonal Antibody, M167-mAb (CalBioReagents) Anti-Human PSA, Free Monoclonal Antibody, | Mouse Anti-Human Free-PSA Monoclonal Antibody, M217 (CalBioReagents) | Prostate Specific Antigen-Free (PSA-Free), Cat#MBS537477, (MyBioSource.com) |

TABLE 1-continued

Assay reagents applied in the assays for PSA, free-PSA and pro-PSA.

| Biomarker | Capture Antibody To be coated on bead sensors | Detection Antibody To be conjugated to Alexafluor488 | Standard Antigen For proof of concept ad dose curve |
|---|---|---|---|
| Pro PSA | Cat#MP014 (Full Moon Technologies) N/A yet | N/A yet | N/A yet |

The initial prostate cancer-specific diagnostic test here described employed a minimum of 3 beads dedicated to each of the biomarkers targeted. This level of bead redundancy was shown previously to increase the statistical significance, and hence precision and accuracy of the measurements.

The remaining beads were conjugated to isotypic antibodies irrelevant to analytes and serve as negative controls. These beads were not expected to capture any of the analytes and as expected did not produce a signal in response to the cocktail mixture of the analyte-specific fluorescent detection antibodies. These negative control beads also served as baseline calibrators for the exposure setting on the charge coupled device (CCD) of the imaging station.

Proof of concept for single analyte test was PSA was achieved (data not shown) using a prototype device that applied reagents shown in Table 1. The beads were coupled to monoclonal antibody M165 (CalbioReagents) and were arrayed on the microchip, along with two calibrator beads and a negative control bead, and sequentially exposed to PSA (100 ng/mL) and monoclonal detection antibody M164-AlexaFluor®488 to develop a PSA-specific signal. This signal was absent in the negative control beads, as well as on the PSA sensors when the assay was repeated in the absence of PSA (0 ng/mL condition). Similar proof of concept was demonstrated for free-PSA using the above approach (data not shown).

The above proof of concept studies used commercially available antibodies, as indicated in Table 1. However, there are a great many anti-PSA antibodies available on the market, and any of these can be selected and tested for reproducible results. All that is needed for a reliable sandwich assay is that the capture and detection antibodies are matched and, hence, bind to differing, non-overlapping epitopes. Further, a multi-marker test can either use different conjugation dyes or can place the different markers in different spots in the array, position thus indicating what biomarker is being tested.

Example 1

Multiplex Test

Figure 2:
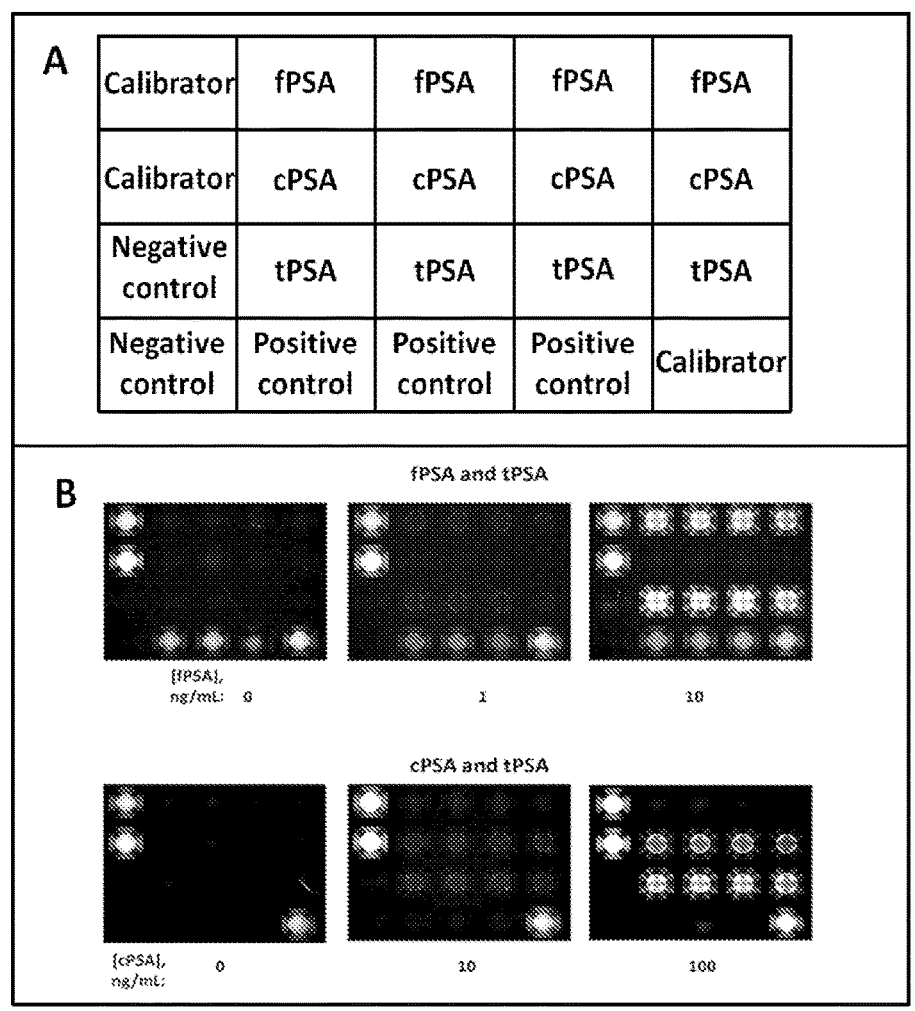
FIG. 2A. An exemplary bead array for prostate cancer targets the simultaneous measurement of total PSA, complexed PSA and free PSA. In addition to the 4-bead redundancy dedicated to the measurement of the fore-mentioned analytes, the array includes calibrator beads, which serve for the baseline calibration of the analyzer, as well as negative controls beads (coupled to antibody irrelevant to the analytes), serving as indicators of the specificity of the antigen-antibody reactions completed within the lab card. The same beads allow for the identification of heterophilic antibodies that may be present in the sample. Lastly, positive control beads recognize and confirm the delivery of anti-PSA detection antibody to the array, and a series of cPSA and free-PSA of known amounts allows the preparation of a standard curve. These standards can be mixed, or provided separately, depending on the detector antibody used.
FIG. 2B. Proof of concept results for the detection of free PSA, complexed PSA and total PSA is shown, wherein the array is magnified and photographed.

Sandwich antibody assays have been developed and multiplexed as a panel (FIG. 2) using reagents shown in Table 2. These were identified as optimal antibody reagents towards tests for PSA, complexed-PSA, and free-PSA on the P-BNC system. The promising biomarker complexed-PSA was developed as a replacement of the biomarker pro-PSA, because the reagents for pro-PSA (pending FDA approval) have not yet been released by the sole provider, but either marker can be used. The chip panel also includes internal (positive and negative) controls, as well as calibrators for the optical sensor analyzer.

TABLE 2

Optimized Reagents

| Biomarker | Capture Antibody Coated on bead sensors | Standard Antigen For proof of concept and dose curve | Detection Antibody Conjugated to Alexafluor488 |
|---|---|---|---|
| Total PSA | Total PSA mAb Clone M212091, Cat# 10-P20C (Fitzgerald) | Artificial combinations of free PSA and PSA-ACT standards in PBS ProMedDX Patient PSA Serum Samples Sunnylab Patient PSA Serum Samples | Total PSA mAb, Clone 5A6 Cat# MBS311572 (MyBioSource) |
| Free PSA | Free PSA mAb, Cat #M167 (CalBioReagents) | Free PSA, Human Seminal Fluid, Cat# CSI14824A (Cell Sciences) | same |
| Complex PSA (PSA-ACT) | PSA-ACT mAb, Cat# M168 (CalBioReagents) | PSA-ACT complex, Cat# 30-AP13, Human Seminal Fluid (Fitzgerald) | same |

The analyzer used in past studies was a device developed by LABNOW™ (Austin Tex.) and described in Jesse V. Jokerst et al., Programmable Nano-Bio-Chip Sensors: Analytical Meets Clinical Analytical Chemistry, Vol. 82, No. 5, Mar. 1, 2010, among other articles. However, future experiments are expected to use an analyzer by Force Diagnostics™ (Chicago, Ill. and Houston, Tex.). Other devices and systems can be used and are e.g., described in WO2007002480, WO2005083423, WO2004009840, WO2005085796 and US2009215072. Agarose disk chips currently under development and described in PCT/US11/47431, filed Aug. 11, 2011 are expressly incorporated herein by reference.

The Force Diagnostics™ analyzer is portable (weight=~5 kg) and has CCD imaging with magnification. It is run on an AC/DC battery, has fully automated control software, a two-color LED system, and integrated image analysis. Data input is by analyzer or USB keyboard, and the device has three USB connectors for data input and output.

The disposable cartridge was a single use, self-contained, disposable cartridge having about 3 microliter sample volume capacity, and containing 2×500 microliter onboard buffer packs that contained wash and buffer fluids. Sample was applied via an inlet valve and the card inserted into the slot in the FORCE DIAGNOSTICS™ analyzer. Using device actuated microfluidics, the sample travelled to an array of capture antibodies for capturing the analyte(s) of interest, and then stringent wash solutions were passed over the array.

The secondary antibody then travelled over the array and the captured analytes, thus binding the detection antibodies to the captured PSA, and the array was washed again. The detection antibody was labeled with a fluorescent dye, and the CCD camera and magnification detected the signal produced thereby, and the embedded software then calibrated the amount of signal using calibration samples also present in the array and computed the risk of disease based on analyte levels.

Figure 4:
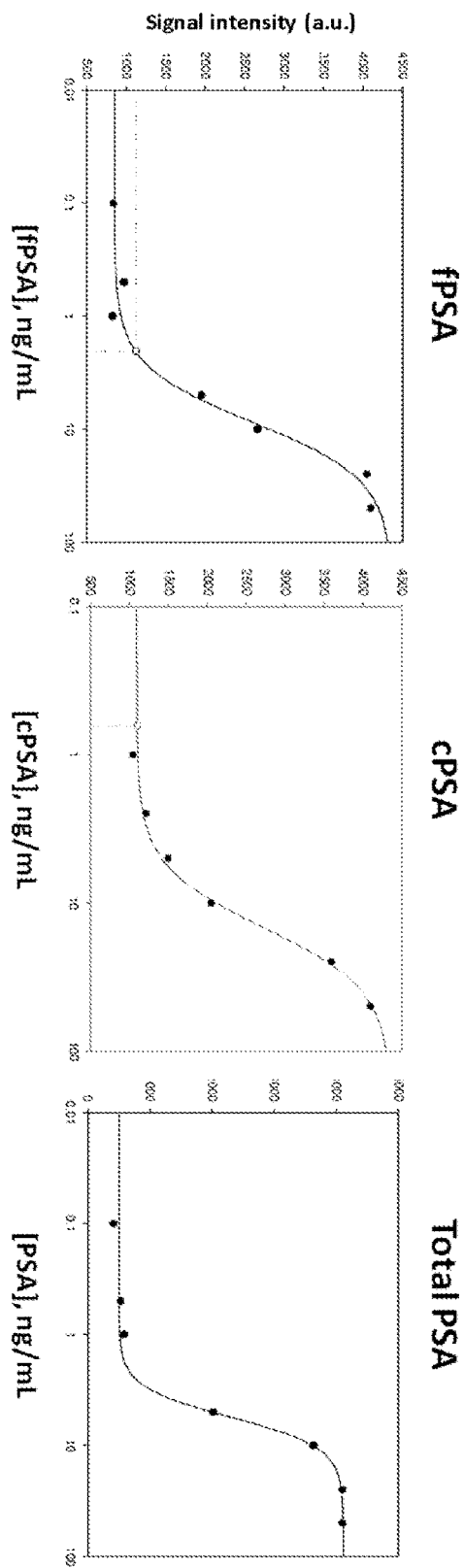
FIG. 4. Typical dose curves for free PSA, complexed PSA and total PSA obtained using the P-BNC system.
Figure 5:
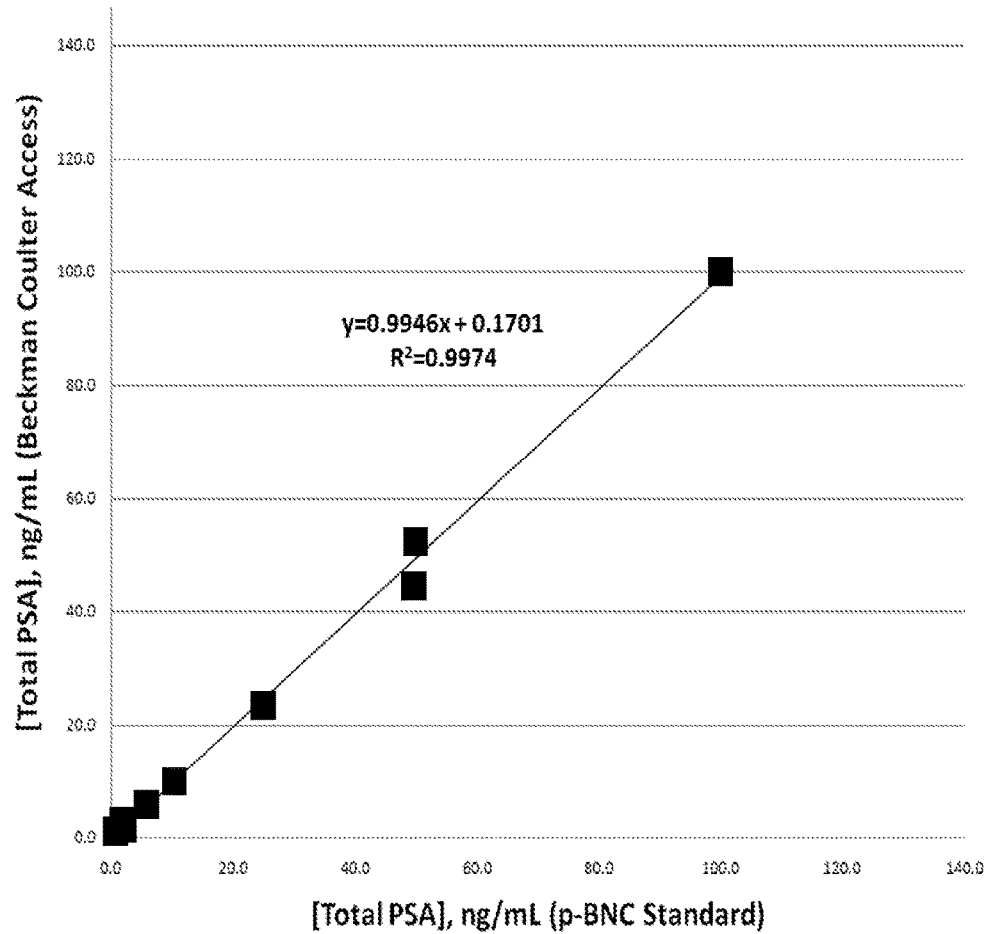
FIG. 5. PSA quality control/standard used in the testing correlates highly with the counterpart standard used by Beckman Access (Quest Diagnostics) ($r^2=0.997$). Similar findings were derived for the free PSA standard ($r^2=0.996$).

Fully-automated macros/algorithms for the analysis of images acquired for each test were developed, allowing for their conversion into quantitative PSA protein information. These advancements and capabilities culminated in the generation of assay performance data that include dose curves (FIG. 4) demonstrating advanced assay performance characteristics, such as low limits of detection (0.1 ng/mL for free-PSA and total PSA, and 0.63 ng/mL for cPSA) and wide assay ranges extending four orders of magnitude, and high precision values for these prostate cancer specific tests (Table 3). Quality controls intended for use during the pilot study (see below) were also established and validated ($r^2=0.99$) with those used by Quest Diagnostics (FIG. 5).

TABLE 3

Assay Characteristics of the multiplexed fPSA, cPSA and tPSA test.

| Assay | Limit of Detection (ng/mL) | Assay Range (ng/mL) | Precision (% CV) |
|---|---|---|---|
| fPSA | 0.1 | 0.1-100 | 5.2 |
| cPSA | 0.63 | 0.63-100 | TBD* |
| tPSA | 0.1 | 0.1-100 | 10.5 |

Figure 6:
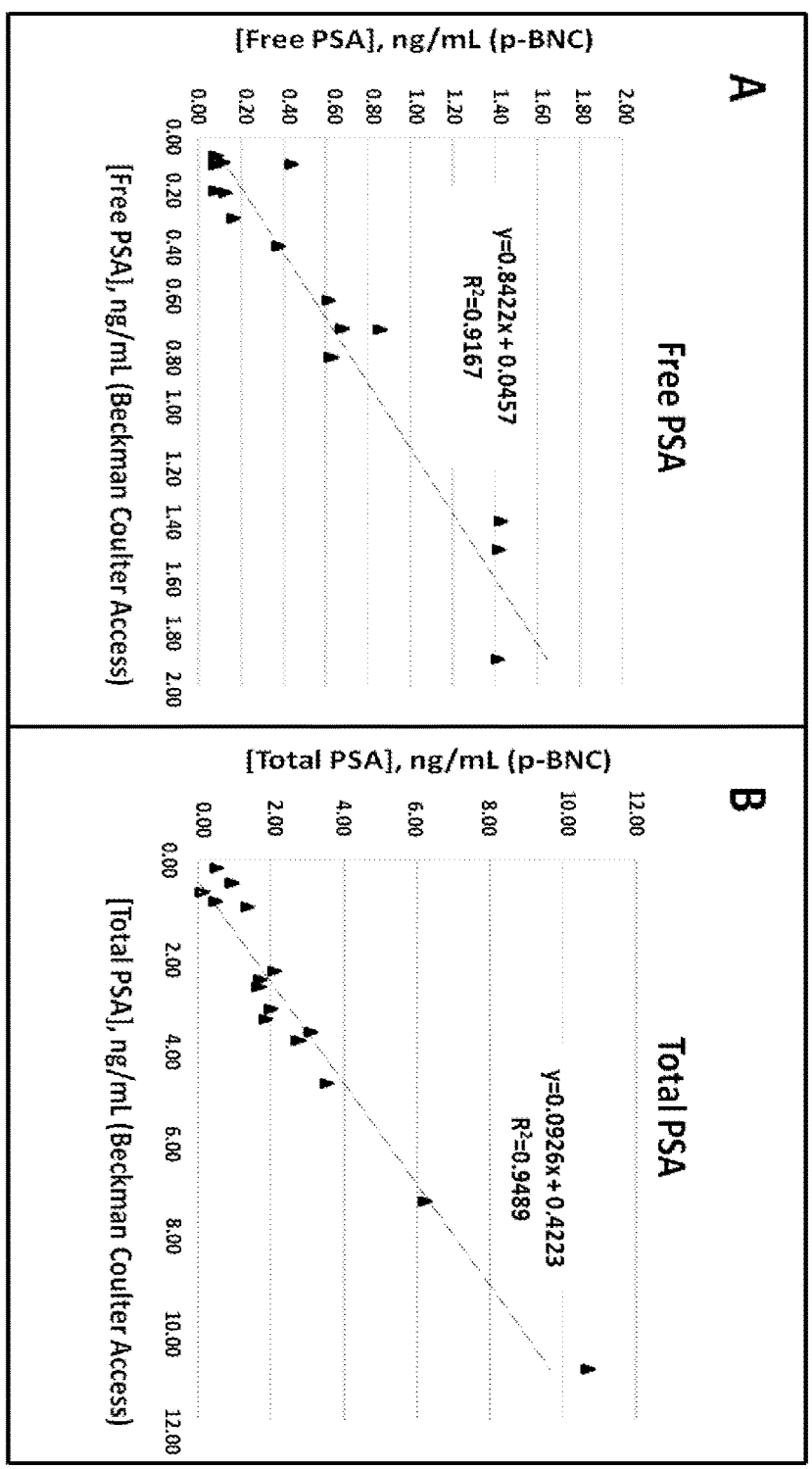
FIG. 6A-B. Correlation between P-BNC test and Quest Diagnostics (Beckman Access)-based measurements of free PSA-$r^2=0.917$ (A) and PSA-$r^2=0.949$ (B).

A pilot study for the P-BNC-system-based prostate cancer test was completed. Once the assay reached a critical level of performance, it was validated in a methods comparison study. Patient samples were tested with the multiplexed, point of care prostate cancer panel and results were compared to those accrued at Quest Diagnostics using a laboratory-confined clinical analyzer (that employs ELISA methodology). Data gathered with the point of care assay of the invention correlated highly ($r^2>0.9$) with those achieved with reference method of Beckman Access, an expensive, bulky and laboratory-confined instrument (FIG. 6).

Figure 7:
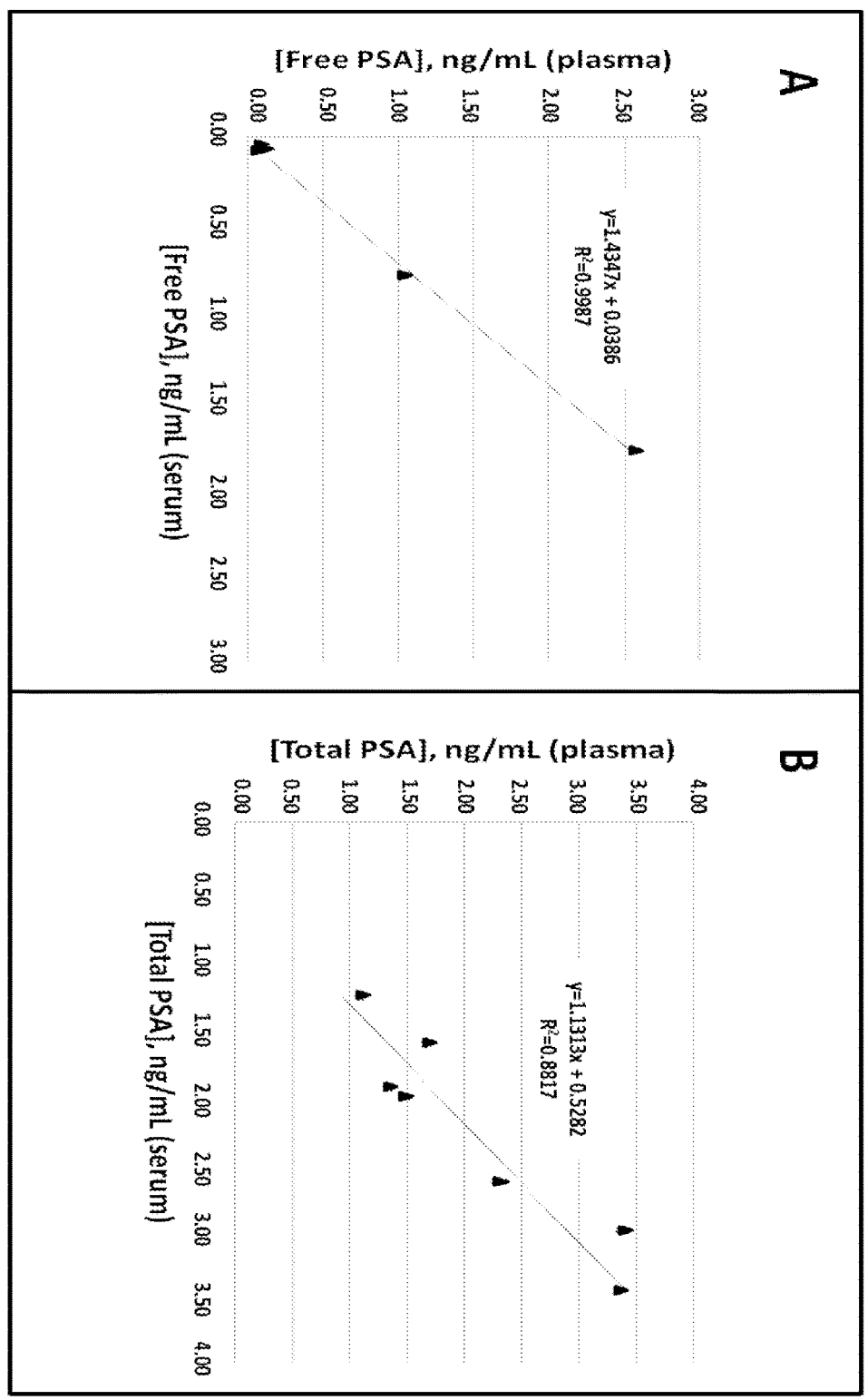
FIG. 7A-B. Correlation between serum and plasma measurements for free PSA (A) and PSA (B) as measured by the P-BNC system. Noted is that numerous low concentration points of free-PSA are superimposed in this graph (n=10).

Further, there was a good correlation in the serum/plasma levels of these biomarkers as measured by the P-BNC system (FIG. 7), serving as a good first step indicator of progress made en route to the transition of these assays from serum, to whole blood and, ultimately, to fingerstick-based point of care testing.

Example 2

Risk Calculator

The Prostate Cancer Prevention Trial Risk Calculator (prostate-cancer-risk-calculator.com) was developed as an outgrowth of the observation that PSA cannot be used as a dichotomous predictor of prostate cancer risk (e.g., PSA<4 ng/mL=normal; PSA>10 ng/mL=elevated), but that PSA is linearly related to risk of cancer as well as risk of high grade, potentially-lethal disease. Thus, researchers developed a multi-variable risk assessment tool that predicts the risk of prostate cancer and risk of high grade disease for an individual patient. This tool is used world-wide for risk assessment of men who are considering prostate biopsy.

More recently, our group added other biomarkers and risk variables (e.g., biomarkers: PCA3, percent free-PSA, proPSA, body mass index (BMI) and finasteride use) to the risk calculator and these have led to more precise and updated risk assessment.

Several of these biomarkers are only approved for certain ranges of PSA. For example, percent free-PSA, an important biomarker that improves risk assessment, is only approved for the PSA range of 4-10 ng/mL. This is because at very low levels of PSA, no additional biomarkers are needed because most patients have a very low risk of cancer. On the other hand, at very high levels (e.g., >10 ng/mL), the patient's risk of prostate cancer and, more importantly, of high-grade, potentially lethal prostate cancer is so high that no additional biomarkers are needed either and the patient needs to have a prostate biopsy regardless of any additional biomarker results.

A challenge for the practitioner who is assessing a patient's risk of prostate cancer is that this assessment is often iterative. For example, the patient is discharged from clinic with a PSA request. If the PSA is in the 4-10 ng/mL range, he is instructed to return to the lab for the, for example, free-PSA test. The provider must then call the patient with the initial results, communicate with the lab to order the test, re-check on the lab results, and then again call the patient.

Because of the extra time required and 'nuisance' factor for sequential tests, efficiencies are sometimes put into place that are costly or are medically inappropriate. One such work-around is to have all patients have both a PSA and free-PSA test. For most patients, this is an unnecessary use of resources, adding $50-100 to the testing to benefit perhaps 6-7% of the group with a PSA between 4-10. Another approach is to simply recommend a prostate biopsy for men in the 4-10 range. This is an even worse outcome as (1) only about 25-30% of these men will have cancer of whom the minority will have biologically-consequential cancer, (2) men for whom a percent free-PSA value would have argued against a prostate biopsy are subjected to this invasive procedure, and (3) all of these men are then subjected to a high-cost procedure with a 2-4% current risk of sepsis.

Figure 3A:
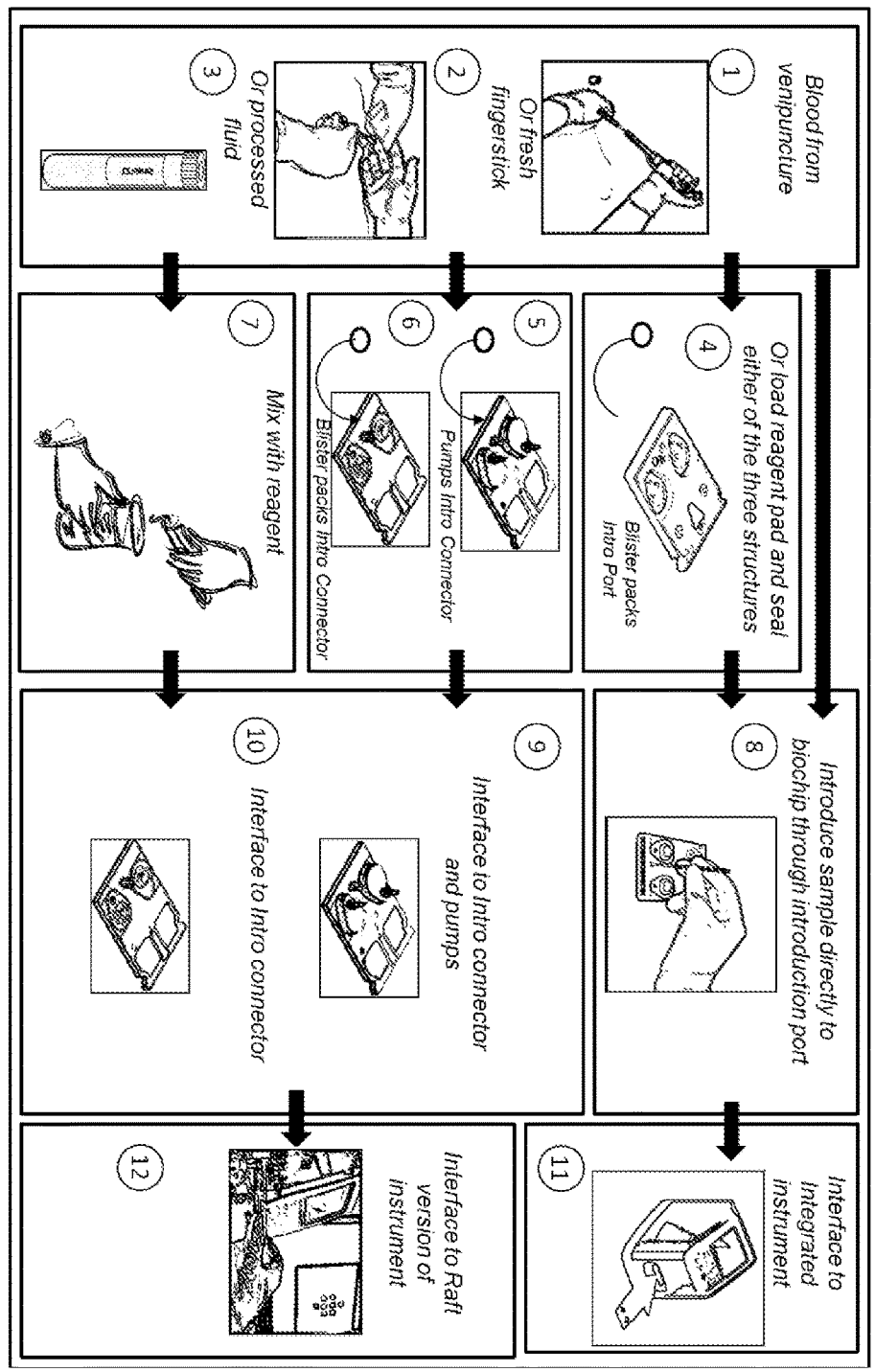
FIG. 3A. Schematic showing the various ways the assay can be run. The fully automated method (2>8>11) envisions applying a blood sample directly to an inlet port, inserting the card into the machine and running the test. However, in our prototype development, various less automated methods have been employed, sometimes using a raft version (prototype) of the analyzer (12). Also, sometimes frozen samples were used, necessitating the use of a prior reagent mixing step (3, 7).
Figure 3B:
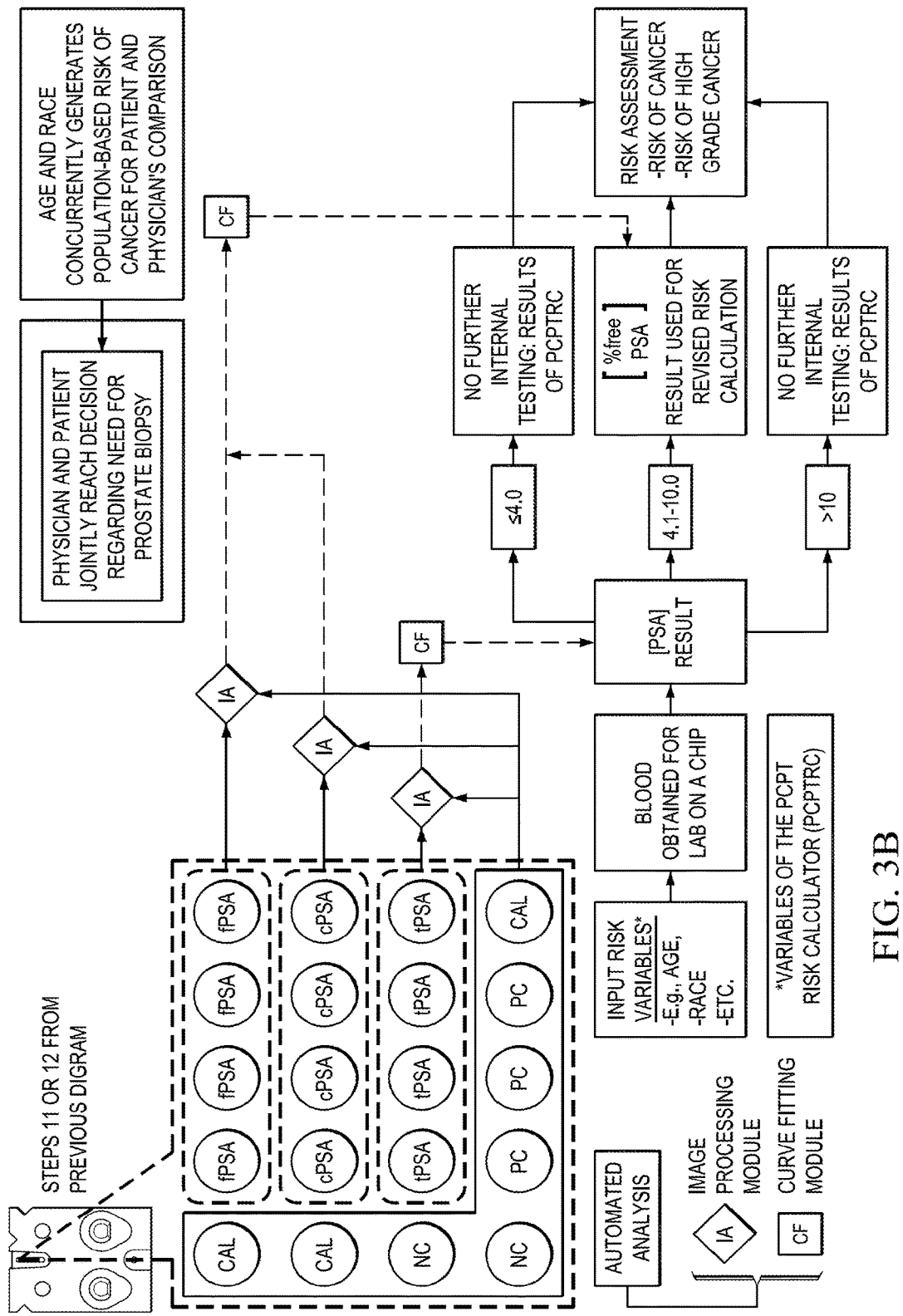
FIG. 3B. The screening algorithm for prostate cancer.

What is proposed in the first iteration of our point of care risk assessment process is described in the flow chart at FIG. 3. The medical practitioner enters risk variables into the input screen of the portable analyzer. These include age, race, family history, prior prostate biopsy, rectal exam findings (these can be omitted as the algorithm is valid without this missing data), or other variables such as BMI and history of use of finasteride.

Then, the patient's blood is obtained and placed on/in the device. After the assays are concurrently run, the internal algorithm first measures and integrates the PSA results. For patients with a PSA of 4 or below or above 10, the %-free-PSA value is hidden and not incorporated in the decision tool and the result is reported. The result will include the following in this situation: PSA, Risk of prostate cancer, risk of high grade prostate cancer.

For the patient whose PSA is between 4 and 10, the results of the percent free-PSA assay is then incorporated into the algorithm and the following results are reported: PSA, percent free-PSA, risk of prostate cancer, risk of high grade prostate cancer. In this latter situation, not only does the percent free-PSA help discriminate higher from lower-risk patients but, at the present time, it is approved by the FDA for this indication and most insurance will reimburse for its measurement.

Finally, a challenge for patients previously has been for them to understand their risk of prostate cancer in the context of a relatively high population risk. The on-board calculations of the portable analyzer will then provide to the patient an age and race-adjusted risk, comparing his own risk with that of a similar man his age and his race. Thus, if a Caucasian man sees that he has a 10% risk of prostate cancer at the age of 70 he may be concerned that this is a one-in-ten risk of cancer and that he ought to have a prostate biopsy. Using population-based studies, we could then show him data that the average man his age has a 15-20% risk of prostate cancer and that, with a 10% risk, his risk is actually lower than the average man. This would then relieve anxiety in some men, while in other men with higher risks, help them to understand why they may opt for further testing.

This methodology can be updated using more sophisticated systems as well. We have previously demonstrated that it is possible to use more comprehensive assessments for individual men to determine the additional utility of additional biomarkers such as percent free-PSA, complexed PSA, proPSA, and PCA3.

Figure 8:
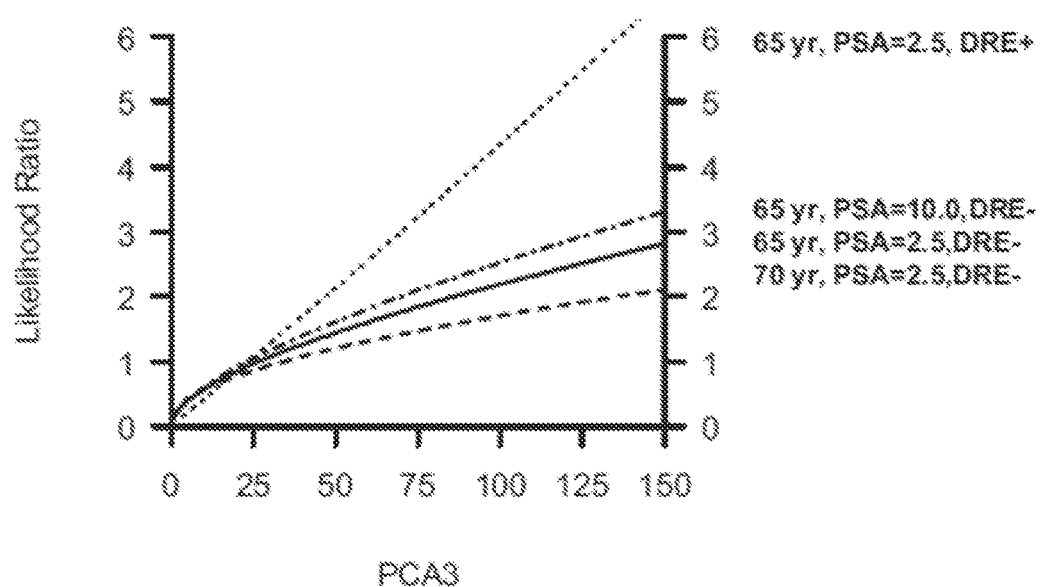
FIG. 8. Likelihood ratio by PCA value and percentile for white males with no prior biopsy.

FIG. 8, for example, shows that for a 70 year old man with a normal DRE and PSA of 2.5, the PCA3 value helps to discriminate to an extent across the range of values but the magnitude is perhaps a 3-fold difference in risk. Conversely, if the man is 65 and has an abnormal DRE, there may be a 6-fold difference in the likelihood of cancer across the range of PCA3.

The calculator is in principle only applicable to men under the following restrictions: Age 55 or older, no previous diagnosis of prostate cancer, and DRE and PSA results less than 1 year old. The following calculation is used when a simple risk calculation is employed:

| Variables: |
| --- |
| PSA = PSA concentration in ng/mL |
| FAMHIST = 1 if father, brother or son ever had prostate cancer; 0 otherwise |
| DRE = 1 if digital rectal exam positive, suspicious for prostate cancer; 0 otherwise |
| PRIORBIOP = 1 if ever a prior prostate biopsy was performed; 0 otherwise |
| AGE = age in years |
| AA = 1 if African American; 0 otherwise |
| $BM_{x1...x(n-4)}$ = Additional Biomarkers that may be used |
| $a_{0...n}$ = weighing coefficients for biomarkers listed above as well as additional candidates $BM_{x1} \ldots BM_{x(n-5)}$ used in logistic regression calculator for PCA |
| $b_{0...n}$ = weighing coefficients for biomarkers listed above as well as additional candidates $BM_{x1} \ldots BM_{x(n-6)}$ used in logistic regression calculator for HG |

| Equations: |
| --- |
| Prostate Cancer Risk = $1/[1 + \exp(-PCA)]$ |
| PCA = $a_0 + a_1 \times \log(PSA) + a_2 \times FAMHIST + a_3 \times DRE + a_4 \times PRIORBIOP + a_5 \times \log(fPSA) + a_6 \times BM_{x1} + a_7 \times BM_{x2} + \ldots + a_n \times BM_{x(n-5)}$ |
| $a_0 = -1.7968$; $a_1 = 0.8488$; $a_2 = 0.2693$; $a_3 = 0.9054$; $a_4 = -0.4483$ |
| thus PCA = $-1.7968 + 0.8488 \times \log(PSA) + 0.2693 \times FAMHIST + 0.9054 \times DRE - 0.4483 \times PRIORBIOP$ |
| High-Grade Risk = $1/[1 + \exp(-HG)]$ |
| HG = $b_0 + b_1 \times \log(PSA) + b_2 \times AGE + b_3 \times DRE + b_4 \times AA + b_5 \times PRIORBIOP + b_6 \times \log(fPSA) + b_7 \times BM_{x1} + b_8 \times BM_{x2} + \ldots + b_n \times BM_{x(n-6)}$ |
| $b0 = -6.2461$; $b_1 = 1.2927$; $b_2 = 0.0306$; $b_3 = 1.0008$; $b_4 = 0.9604$; $b_5 = 0.3634$ |
| thus HG = $-6.2461 + 1.2927 \times \log(PSA) + 0.0306 \times AGE + 1.0008 \times DRE + 0.9604 \times AA - 0.3634 \times PRIORBIOP$ |

** Work is still ongoing to determine the appropriate values for a5 and b6.

The risk calculator is available at prostate-cancer-risk-calculator.com, but may of course be modified by adding in additional biomarkers, or the weight of one or more factors may be adjusted as new data becomes available, or as additional bio markers are added to the analysis. Another more complex risk calculator is provided as follows:

```
R Code PCPT
#PCPT risk calculator, 95% confidence interval
#psa: psa in ng/mL
#dre: 1 if abnormal suspicious for cancer; 0 otherwise
#priorbiop: 1 if prior negative biopsy; 0 if no prior negative biopsy
#famhist: 1 if first degree positive family history; 0 otherwise
risk <- function(psa,famhist,dre,priorbiop)
{
#Order: Intercept lpsa fampca dre priorbiop
betas <- c(-1.796793671,0.8488458598,0.2692952172,0.9054345656,-0.448331957)
x=matrix(c(1,log(psa),famhist,dre,priorbiop),ncol=1)
pred=betas%*%x
return(exp(pred)/(1+exp(pred)))
}
risk.interval <- function(psa,famhist,dre,priorbiop)
{
#Order: Intercept lpsa fampca dre priorbiop
betas <- c(-1.796793671,0.8488458598,0.2692952172,0.9054345656,-0.448331957)
varbetas <- matrix(
c(0.0024863856,-0.001228313,-0.001375148,-0.001352417,-0.000654073,
-0.001228313,0.0021456952,-0.000120004,0.0002151793,-0.001002991,
-0.001375148,-0.000120004,0.0074681393,0.0000445035,0.0000268546,
-0.001352417,0.0002151793,0.0000445035,0.0099989763,-0.001093113,
-0.000654073,-0.001002991,0.0000268546,-0.001093113,0.0100889794),
nrow=5,ncol=5,byrow=T)
x<-matrix(c(1,log(psa),famhist,dre,priorbiop),ncol=1)
pred=betas%*%x
phat=exp(pred)/(1+exp(pred))
```

```
dpdbeta=matrix(c(x)*exp(pred)/(1+exp(pred))^2,ncol=1)
varphat=t(dpdbeta)%*%varbetas%*%dpdbeta
return(c(phat-1.96*sqrt(varphat),phat+1.96*sqrt(varphat)))
}
#PCPT high grade risk calculator, 95% confidence interval
#psa: psa in ng/mL
#age: age in years
#dre: 1 if abnormal suspicious for cancer; 0 otherwise
#priorbiop: 1 if prior negative biopsy; 0 if no prior negative biopsy
#aa: 1 if African American; 0 otherwise
hgrisk <- function(psa,age,dre,priorbiop,aa) {
#Order: Intercept lpsa age dre priorbiop aa
betas=matrix(c(-6.2461,1.29267,0.030623,1.00083,-0.36335,0.96039),nrow=1)
x=matrix(c(1,log(psa),age,dre,priorbiop,aa),ncol=1)
pred=betas%*%x
return(exp(pred)/(1+exp(pred)))
}
#PCPT high grade risk 95% confidence interval
hgrisk.interval <- function(psa,age,dre,priorbiop,aa) {
#Order: Intercept lpsa age dre priorbiop aa
betas=matrix(c(-6.2461,1.29267,0.030623,1.00083,-0.36335,0.96039),nrow=1)
varbetas=matrix(
c(0.71992,-0.01344,-0.009964,-0.00711, 0.00829,-0.03171,
-0.01344,0.00862,0.000073, 0.00068,-0.00373,-0.00009,
-0.00996,0.00007,0.000141,0.00002,-0.00014,0.00038,
-0.00711,0.00068,0.000015,0.02769,-0.00216,0.00153,
0.00829,-0.00373,-0.000139,-0.00216,0.0323,0.0005,
-0.03171,-0.00009,0.000378,0.00153,0.0005,0.07137),
nrow=6,ncol=6,byrow=T)
x=matrix(c(1,log(psa),age,dre,priorbiop,aa),ncol=1)
pred=betas%*%x
phat=exp(pred)/(1+exp(pred))
dpdbeta=matrix(c(x)*exp(pred)/(1+exp(pred))^2,ncol=1)
varphat=t(dpdbeta)%*%varbetas%*%dpdbeta
return(c(phat-1.96*sqrt(varphat),phat+1.96*sqrt(varphat)))
}
#PCPT finasteride risk
#Here if check yes to finasteride
finrisk <-function(psa,famhist,dre,priorbiop) {
return(risk(2*psa,famhist,dre,priorbiop))
}
finrisk.interval <- function(psa,famhist,dre,priorbiop) {
return(risk.interval(2*psa,famhist,dre,priorbiop))
}
#PCPT finasteride high graderisk
hgfinrisk <-function(psa,age,dre,priorbiop,aa) {
return(hgrisk(2*psa,age,dre,priorbiop,aa))
}
hgfinrisk.interval <- function(psa,age,dre,priorbiop,aa) {
return(hgrisk.interval(2*psa,age,dre,priorbiop,aa))
}
#PCPT risk incorporating PCA3
#pca3: urine marker PCA3, no units
pca3risk=function(pca3,psa,famhist,dre,priorbiop,age) {
meanco= -.6915-.1137*log(psa)+.0577*age-.3345*dre+.1260*priorbiop
meanca= 1.1926-.0836*log(psa)+.0376*age+.1055*dre+.0658*priorbiop
sdco=1.0191
sdca=1.0366
lr=dnorm(log(pca3),meanca,sdca)/dnorm(log(pca3),meanco,sdco)
priorrisk=risk(psa,famhist,dre,priorbiop)
po=lr*priorrisk/(1-priorrisk)
pr=po/(1+po)
return(pr)
}
#PCPT risk adjusted for BMI
#unit: 0=standard, 1=metric
#height: height in inches or cm
#weight: weight in pounds or kg
bmirisk=function(unit,height,weight,psa,famhist,dre,priorbiop,race) {
if (unit==0) { bmi= weight*703/ height^2 } else
{ bmi= weight*10000/ height^2 }
if (bmi<25) {adjpsa=psa}
if (bmi>=25 & bmi<30) {adjpsa=psa*1.09}
if (bmi>=30 & bmi<35) {adjpsa=psa*1.20}
if (bmi>=35 & bmi<40) {adjpsa=psa*1.50}
if (bmi>=40) {adjpsa=psa*1.71}
return(risk(adjpsa,famhist,dre,priorbiop))
}
bmirisk.interval=function(unit,height,weight,psa,famhist,dre,priorbiop,race) {
```

```
if (unit==0) { bmi= weight*703/ height^2 } else
{ bmi= weight*10000/ height^2 }
if (bmi<25) {adjpsa=psa}
if (bmi>=25 & bmi<30) {adjpsa=psa*1.09}
if (bmi>=30 & bmi<35) {adjpsa=psa*1.20}
if (bmi>=35 & bmi<40) {adjpsa=psa*1.50}
if (bmi>=40) {adjpsa=psa*1.71}
return(risk.interval(adjpsa,famhist,dre,priorbiop))
}
#PCPT high grade risk adjusted for BMI
#unit: 0=standard, 1=metric
#height: height in inches or cm
#weight: weight in pounds or kg
bmihgrisk=function(unit,height,weight,psa,age,dre,priorbiop,aa) {
if (unit==0) { bmi= weight*703/ height^2 } else
{ bmi= weight*10000/ height^2 }
if (bmi<25) {adjpsa=psa}
if (bmi>=25 & bmi<30) {adjpsa=psa*1.09}
if (bmi>=30 & bmi<35) {adjpsa=psa*1.20}
if (bmi>=35 & bmi<40) {adjpsa=psa*1.50}
if (bmi>=40) {adjpsa=psa*1.71}
return(hgrisk(adjpsa,age,dre,priorbiop,aa))
}
bmihgrisk.interval=function(unit,height,weight,psa,age,dre,priorbiop,aa) {
if (unit==0) { bmi= weight*703/ height^2 } else
{ bmi= weight*10000/ height^2 }
if (bmi<25) {adjpsa=psa}
if (bmi>=25 & bmi<30) {adjpsa=psa*1.09}
if (bmi>=30 & bmi<35) {adjpsa=psa*1.20}
if (bmi>=35 & bmi<40) {adjpsa=psa*1.50}
if (bmi>=40) {adjpsa=psa*1.71}
return(hgrisk.interval(adjpsa,age,dre,priorbiop,aa))
}
#PCPT risk incorporating both %freePSA and [-2]proPSA
#perfreepsa: percent free PSA
#propsa: [-2]proPSA in pg/mL
postrisk=function(perfreepsa,propsa,psa,famhist,dre,priorbiop,age) {
#order %freePSA, [-2]proPSA
newmarkers=matrix(c(log(perfreepsa),log(propsa)),nrow=2)
meanco=matrix(c(3.276295183−
0.234577552*log(psa)+0.002135001*age,2.438274781+0.57138
1464*log(psa)−0.007579198*age),nrow=2)
meanca=matrix(c(2.66738151−
0.36519414*log(psa)+0.01103519*age,1.38475606+0.62748815*
log(psa)+0.00610934*age),nrow=2)
varco=matrix(c(0.12784019,0.09661401,0.09661401,0.18780600),nrow=2)
varca=matrix(c(0.1793767,0.1207655,0.1207655,0.2310282),nrow=2)
distco=newmarkers−meanco
distca=newmarkers−meanca
loglr=−0.5*(log(det(varca))−log(det(varco))+t(distca)%*%solve(varca)%*%distca−t(dist
co)%*%solve(varco)%*%distco)
lr=exp(loglr)
priorrisk=risk(psa,famhist,dre,priorbiop)
po=lr*priorrisk/(1−priorrisk)
pr=po/(1+po)
return(pr)
}
#PCPT risk incorporating %freePSA
#%freePSA: units in percent
perfreepsarisk=function(perfreepsa,psa,famhist,dre,priorbiop,age) {
meanco=3.276−0.235*log(psa)+0.002*age
meanca=2.667−0.365*log(psa)+0.011*age
sdco=sqrt(0.128)
sdca=sqrt(0.179)
lr=dnorm(log(perfreepsa),meanca,sdca)/dnorm(log(perfreepsa),meanco,sdco)
priorrisk=risk(psa,famhist,dre,priorbiop)
po=lr*priorrisk/(1−priorrisk)
pr=po/(1+po)
return(pr)
}
#PCPT risk incorporating [-2]proPSA
#[-2]proPSA: units in pg/mL
propsarisk=function(propsa,psa,famhist,dre,priorbiop,age) {
meanco=2.438+0.571*log(psa)−0.008*age
meanca=1.385+0.627*log(psa)+0.006*age
sdco=sqrt(0.188)
sdca=sqrt(0.231)
lr=dnorm(log(propsa),meanca,sdca)/dnorm(log(propsa),meanco,sdco)
priorrisk=risk(psa,famhist,dre,priorbiop)
```

```
po=lr*priorrisk/(1-priorrisk)
pr=po/(1+po)
return(pr)
}
```

The following references are incorporated by reference herein in their entirety.

PCT/US11/47431, filed Aug. 11, 2011.

Goodey et al., Development of Multianalyte Sensor Arrays Composed of Chemically Derivatized Polymeric Microspheres Localized in Micromachined Cavities J. Amer. Chem. Soc., 123(11):2559-2570, 2001.

Christodoulides et al., Application of microchip assay system for the measurement of C-reactive protein in human saliva Lab. Chip, 5(3):261-9, 2005.

Thompson I M, et al., Prevalence of Prostate Cancer among Men with a Prostate-Specific Antigen Level≤4.0 ng per Milliliter New Engl J Med 2004; 350:2239-46.

Thompson I M, et al., Assessing prostate cancer risk: results from the Prostate Cancer Prevention Trial. J Natl Cancer Inst 2006; 98:529-34.

Ankerst D P, et al. Predicting prostate cancer risk through incorporation of prostate cancer gene 3. J Urology 2008; 180:1303-8.

Jesse V. Jokerst et al., Programmable Nano-Bio-Chip Sensors: Analytical Meets Clinical Analytical Chemistry, Vol. 82, No. 5, Mar. 1, 2010.

WO2007002480, WO2005083423, WO2004009840, WO2005085796 and US2009215072.

We claim:

1. A disposable cartridge comprising a planar support having an inlet port fluidly connected to a detection window, said detection window having an array of agarose beads or disks separately conjugated to a first antibody for measuring total PSA, a second antibody for measuring free-PSA and a third antibody for measuring complexed-PSA or pro-PSA, said planar support further comprising at least one closed wash chamber comprising wash fluid and an empty chamber fluidly connected to and downstream of said array for receiving waste fluids, wherein said wash chamber when open is fluidly connected to said array, and wherein said detection window allows visual inspection of said array from above said disposable cartridge.

2. The disposable cartridge of claim 1, said detection window being covered with a transparent cover.

3. The disposable cartridge of claim 1, said array of agarose beads or disks separately conjugated with i) an antibody for free-PSA; ii) an antibody for complexed-PSA, iii) an antibody for total PSA, iv) a series of known amounts of fluorescent dye for instrument calibration; v) a series of known amounts of complexed PSA for calibration; vi) a series of known amounts of free-PSA for calibration; vii) positive control containing anti mouse IgG antibody, which responds to the detection antibody and confirms its delivery to the bead array, and viii) negative control containing an antibody irrelevant to PSA that serves as indicator of the specificity of the antigen-antibody reactions in the cartridge.

4. The disposable cartridge of claim 3, wherein there are at least three agarose beads or disks separately conjugated with each of i) an antibody for free-PSA; ii) an antibody for complexed-PSA, and iii) an antibody for total PSA.

5. The disposable cartridge of claim 3, wherein there are at least four agarose beads or disks separately conjugated with each of i) an antibody for free-PSA; ii) an antibody for complexed-PSA, and iii) an antibody for total PSA.

6. The disposable cartridge of claim 3, further comprising a closed antibody chamber upstream of said array and downstream of said wash chamber, said antibody chamber comprising dry detection antibody labeled with a fluorescent dye, wherein said antibody chamber when opened is fluidly connected to said array and said wash chamber.

7. A disposable cartridge comprising:
(a) a planar support having an inlet port fluidly connected to a detection window;
(b) said detection window having an array of agarose beads or disks therein, said agarose beads or disks being separately conjugated to i) a total PSA capture antibody, ii) a free-PSA capture antibody, iii) a complexed-PSA capture antibody, iv) a series of known amounts of free PSA for calibration; v) a series of known amounts of complexed PSA for calibration; vi) a negative control containing no PSA and no antibody for PSA;
(c) at least one closed wash fluid chamber and a closed antibody chamber comprising dry detection antibody labeled with a fluorescent dye for detecting any captured PSA, wherein said closed chambers when open are fluidly connected and upstream of said array and wherein said wash fluid chamber is upstream of said antibody chamber; and
(d) an empty chamber fluidly connected and downstream of said array for receiving waste fluids.

8. The disposable cartridge of claim 7, wherein said planar support is plastic.

9. The disposable cartridge of claim 7, wherein said array of agarose beads or disks is contained on a separate removable chip.

10. The disposable cartridge of claim 7, wherein said detection window has a transparent cover.

* * * * *